United States Patent [19]
Betts et al.

[11] Patent Number: 5,405,510
[45] Date of Patent: Apr. 11, 1995

[54] PORTABLE ANALYTE MEASURING SYSTEM FOR MULTIPLE FLUID SAMPLES

[75] Inventors: Ronald E. Betts, La Jolla; Douglas R. Savage, Del Mar; Matthew J. Leader, Laguna Niguel, all of Calif.

[73] Assignee: PPG Industries, Inc., Pittsburgh, Pa.

[21] Appl. No.: 61,969

[22] Filed: May 17, 1993

Related U.S. Application Data

[63] Continuation-in-part of Ser. No. 885,096, May 18, 1992, abandoned.

[51] Int. Cl.$^6$ ............................................. G01N 27/26
[52] U.S. Cl. .......................... 204/153.1; 204/153.12; 204/403; 204/409; 204/412; 204/416; 204/415; 204/435; 435/817; 435/291; 422/58; 422/61; 422/62; 422/63; 422/68.1; 422/82.03; 422/80
[58] Field of Search ............... 204/403, 409, 412, 416, 204/415, 422, 153.1, 435, 153.12; 128/635; 422/58, 61, 62, 63, 68.1, 82.03, 80; 435/291, 817

[56] References Cited

U.S. PATENT DOCUMENTS

| | | | |
|---|---|---|---|
| 3,000,805 | 9/1961 | Carrit et al. | 204/195 |
| 3,049,118 | 8/1962 | Arthur et al. | 128/2 |
| 3,088,905 | 5/1963 | Glover | 204/195 |
| 3,497,442 | 2/1970 | Vincent | 204/195 |
| 3,681,255 | 8/1972 | Wilfore | 252/406 |
| 3,912,614 | 10/1975 | Spracklen et al. | 204/195 B |
| 4,133,735 | 1/1979 | Afromowitz et al. | 240/195 G |
| 4,454,007 | 6/1984 | Pace | 204/1 T |
| 4,654,127 | 3/1987 | Baker et al. | 204/1 T |
| 4,734,184 | 3/1988 | Burleigh et al. | 204/409 |
| 4,786,394 | 11/1988 | Enzer et al. | 204/401 |

(List continued on next page.)

FOREIGN PATENT DOCUMENTS

| | | |
|---|---|---|
| 0015075 | 9/1980 | European Pat. Off. |
| 0027385 | 4/1981 | European Pat. Off. |
| 0306158 | 3/1989 | European Pat. Off. |
| 0351516 | 1/1990 | European Pat. Off. |
| WO85/02257 | 5/1985 | WIPO |

OTHER PUBLICATIONS

"Technical Note: Catheter-tip Electrode for Continuous Measurement of pO$_2$ and pCO$_2$", Medical & Biological Engineering & Computing, 1978, pp. 599-600.

"Quality Control in Blood pH and Gas Analysis by Use of a Tonometered Bicarbonate Solution and Duplicate Blood Analysis", *Clinical Chemistry Journal* by Robert W. Burnett, (1981) vol. 27, No. 10, pp. 1761-1764 (abstract).

(List continued on next page.)

*Primary Examiner*—Kathryn Gorgos
*Assistant Examiner*—Bruce F. Bell
*Attorney, Agent, or Firm*—Kenneth J. Stachel

[57] ABSTRACT

A portable, ready-for-use analyte measuring device is provided for the measurement of multiple sequential fluid samples. The device has a disposable cartridge, a calibrating fluid external to the cartridge and an analyzer. The cartridge has a housing, inlet for introduction of fluids into the housing, flow cell in fluid connection with the inlet, a waste collection area or reservoir in fluid connection to receive fluids from the flow cell, and at least one flow control means in fluid connection with the reservoir. The flow cell has a flow-through channel with one or more hydrated sensors arranged along the channel that has fluid therein. Also the flow cell has one or more spaced-apart reference electrode containment spaces in conductive contact with a contained quantity of reference fluid for the number of multiple sequential tests for the cartridge. The reference electrode containment space is spaced apart from but in conductive relation with the one or more sensors. The flow cell also has an electric circuit attached for electrical conduction to the one or more sensors and reference electrode and which is electrically isolated from the fluid in the channel. The multi-test device also has signal conveyor connected to the electric circuit of the flow cell to transmit signals responsive to the fluids contacting the sensors to the analyzer. Both the cartridge and the calibrating fluid are associated with an encoded information carrier for sensor performance parameters and calibrant analyte concentrations for inputting into the encoded information reader of the analyzer.

36 Claims, 7 Drawing Sheets

U.S. PATENT DOCUMENTS

| | | | |
|---|---|---|---|
| 4,818,361 | 4/1989 | Burgess et al. | 204/406 |
| 4,863,016 | 9/1989 | Fong et al. | 206/210 |
| 4,871,439 | 10/1989 | Enzer et al. | 204/401 |
| 4,929,426 | 5/1990 | Bodai et al. | 204/409 |
| 5,046,496 | 9/1991 | Betts et al. | 128/635 |
| 5,096,669 | 3/1992 | Lauks et al. | 422/62 |

OTHER PUBLICATIONS

Product Information Sheets on SANCAP material Re: HS 035 Heat Seal and HS 015 Heat Seal.

MOCON (Modern Control, Inc.) Product Brochure.

Prospectus re Diametrics Medical, Inc., dated Jun., 1993.

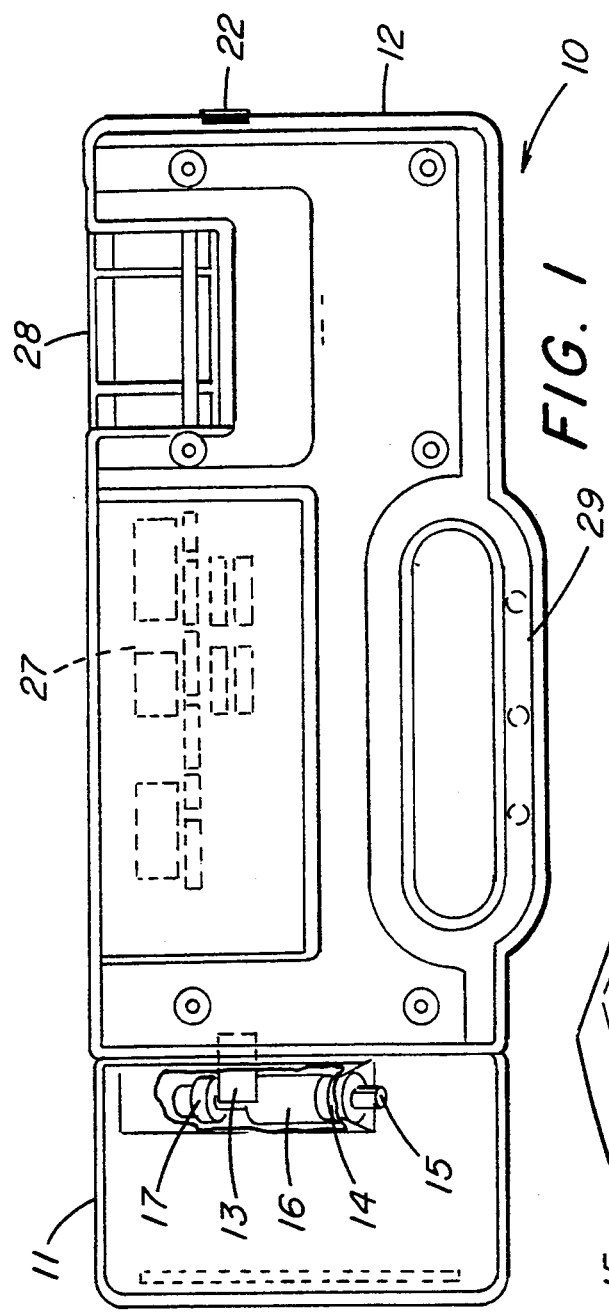
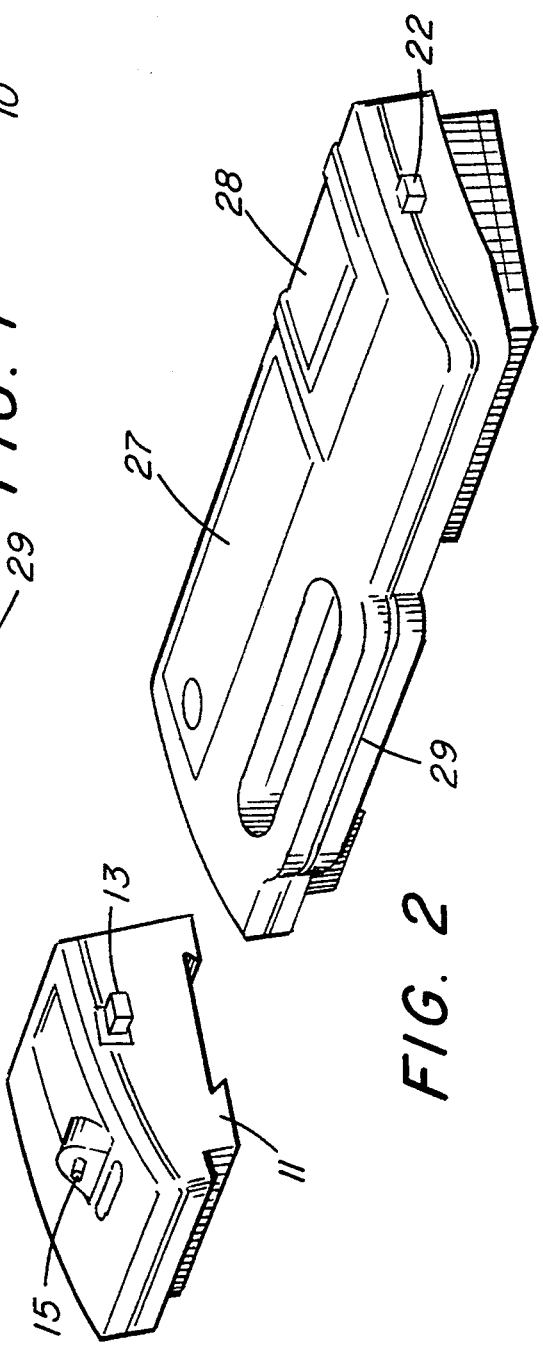

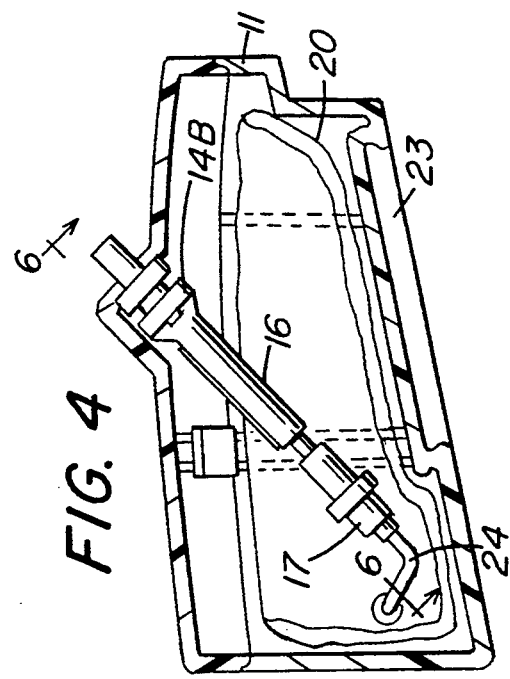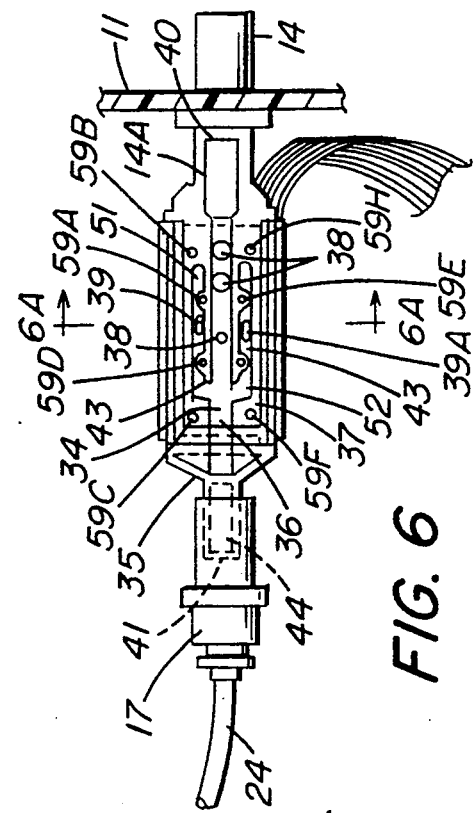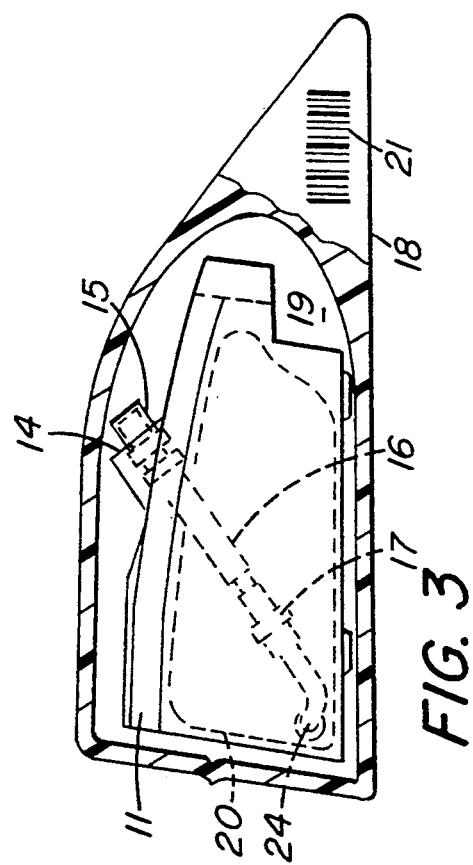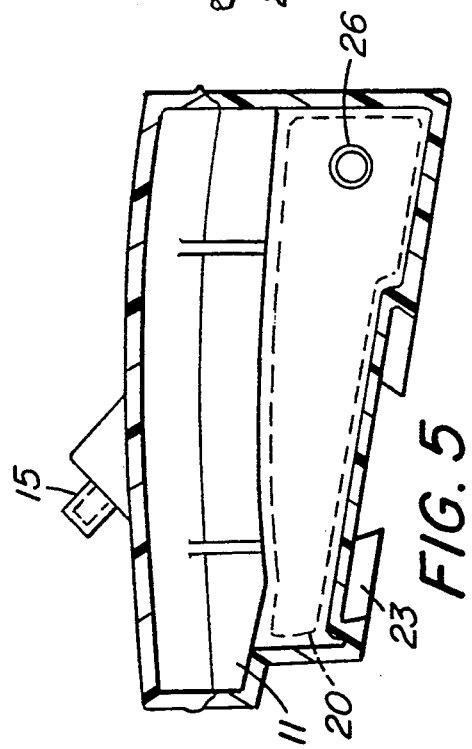

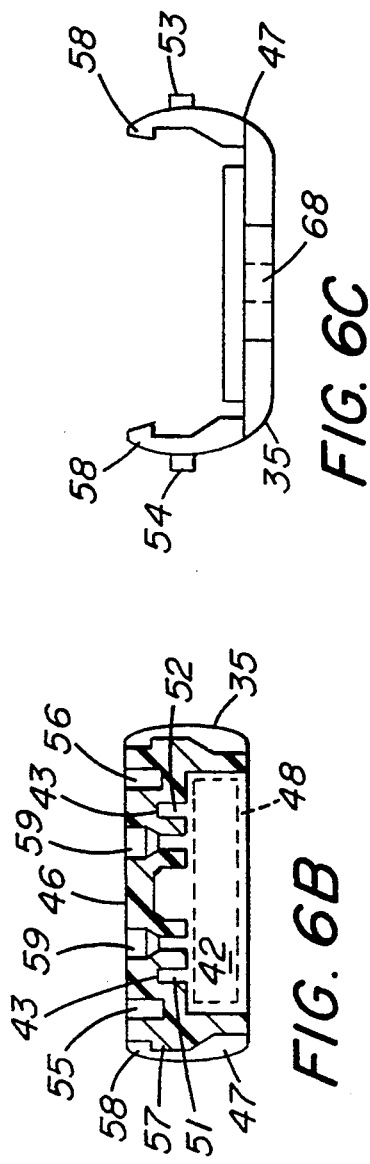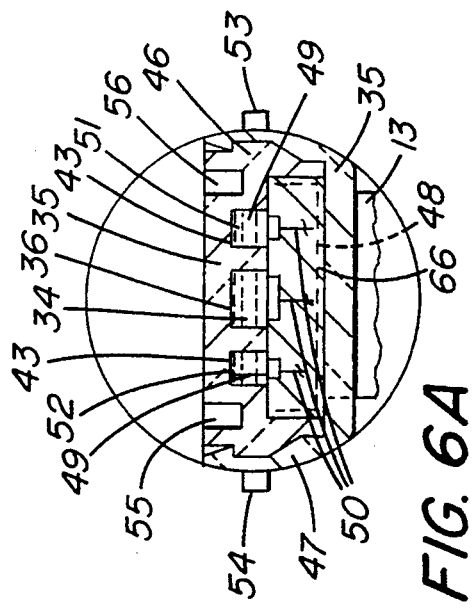

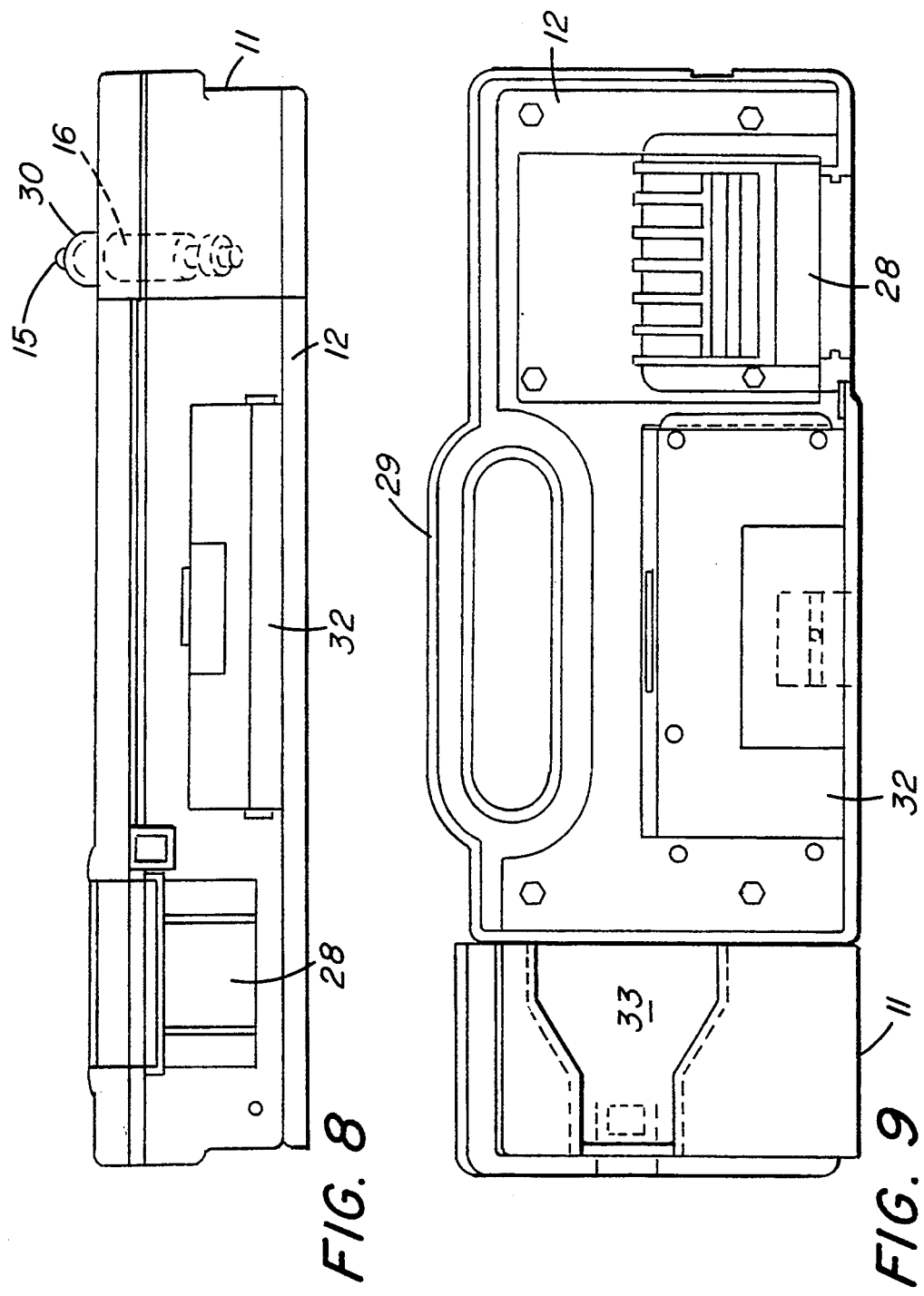

PORTABLE ANALYTE MEASURING SYSTEM FOR MULTIPLE FLUID SAMPLES

This application is a continuation-in-part application of application U.S. Ser. No. 07/885,096, filed May 18, 1992, now abandoned.

The present invention is directed to a system for measuring one or more analytes in a multitude of sequential sample fluids without the necessity for changing any parts of the system. Often times in health care, industrial, commercial and academic settings, it is desirable to analyze fluids for the concentration of one or more analytes. In several of these instances, it is necessary to take a sample of the fluid and transport it to a remote location having an analysis instrument. An example of such a situation is the analysis of chemical constituents of blood and, in particular, the analysis of blood gases. The stationary analyte analyzers allow for sequential analysis of distinct samples, but their lack of portability restricts their use to centralized locations.

A disposable self-calibratible electrode package is disclosed in U.S. Pat. No. 4,871,439 that can be used in a system employing a chemical analysis machine for measuring a plurality of distinct characteristics of bodily fluid samples. The invention of this patent is described as relating to a solid-state electrode or microelectrode sensor apparatus for measuring certain characteristics of an aqueous sample such as bodily fluid or a blood sample. More particularly, the invention is directed to such apparatus which employs such a disposable cartridge containing a sensor or bank of sensors for such characteristics and reagents used to calibrate the sensors. The system is said to provide quick on-site contemporaneous blood chemistry analysis with minimal risk of contamination and which maintains its accuracy over its useful life. The disposable cartridge useful in this system has a bank of electrodes adjacent to a thermals, plate which maintains the test sample at a constant temperature. The electrodes in the cartridge connect to an electrode interface in a blood chemistry analysis machine. The analysis machine selects one of the plurality of the electrical signals generated by the sensors and passes the selected signal to the microprocessor in the machine. The microprocessor converts the signal from analog to digital form suitable for analysis, storage and display. Additionally, the cartridge contains at least one and preferably two containers of reference or calibrating electrolyte solution. This is a solution that serves for purposes of quality control including calibration and is sometimes referred to as calibration solution. The cartridge also has a reservoir suitable to collect waste fluids following assay. Upon insertion of the cartridge, a selection valve in the cartridge connects to a shaft in the machine controlled by the microprocessor to selectively allow either the calibrating solution or the test sample to flow across the electrodes. The driving force for the fluid flow through the cartridge is provided by a peristaltic pump provided with a set of rotatable drive rollers in the machine to pinch exposed portions of tubing against the curved wall of the pump slot on the cartridge. The rotation of the drive rollers is controlled by the microprocessor.

Although the cartridge for the aforedescribed blood gas analysis machine is fairly compact, the machine and the cartridge having its solution containers, pump, and associated tubing is somewhat bulky which reduces the portability of the unit. Also, the sensors that are used are originally unhydrated and must be hydrated before use. This requires a waiting period before each cartridge can be used so that the sensors can hydrate from one of the containerized solutions in the cartridge for production of accurate measurements. This unit may be more suitable for analysis of a continuous blood supply than individual sequential samples.

Recently for certain analytes, disposable analyte analyzers have been proposed. One such device is the clinical chemistry analyzer described in the Patent Cooperation Treaty (PCT) patent application, International Publication No. WO 85/02257 and U.S. Pat. No. 4,654,127 assigned to Sentech Medical Corporation. Another is the device described in U.S. Pat. No. 5,096,669 assigned to I-Stat Corporation. These units have a planar sampling device to hold a sample for analysis when the planar device is inserted into a reader or monitoring device. Although the reading units have a degree of portability, the disposable insertable planar sampling device involves several steps of sample handling. The sample is placed into the planar device and then the device is inserted into the reader. In this day and age of limiting contact with certain chemical samples to be tested, such as bodily fluids, the needs exist to reduce the amount of sample handling but still have disposable units to minimize exposure to certain bodily fluids during analysis.

It is an object of the present invention to provide a portable, fluid analyte measuring device for multiple sequential samples where the device has a ready-for-use, multiple use, disposable cartridge to facilitate use of the device at or near the site of sample generation.

SUMMARY OF THE INVENTION

The aforementioned and other objects gleaned from the following disclosure are accomplished with the portable, ready-for-use analyte measuring device for multiple sequential fluid samples of the present invention. The device has a disposable cartridge, a fluid calibration means external to the cartridge and an analyzer.

The cartridge has a housing, inlet for introduction of fluids into the housing, flow cell in fluid connection with the inlet, a waste collection area or reservoir in fluid connection to receive fluid directly or indirectly from the flow cell, and at least one directional flow control means at least to retard any backflow of fluid from the reservoir.

The inlet for introduction of fluids into the housing of the cartridge extends through to the exterior of the housing. The interior of the housing has a flow cell connected to the inlet or serves as the inlet for fluid flow into the flow cell. The connection to the flow cell is at an opening in the flow cell that forms a channel that runs through the flow cell to a second opening.

In addition to the channel, the flow cell also has a sensor containment area with at least one hydrated sensor, a reference electrode containment area, fluid occupying the channel, and an electric circuit.

In the flow cell, the sensor containment area holds the at least one sensor that is comprised of at least one measuring electrode in sensing relationship to the channel so that the sensor sensingly contacts the fluids that flow through the channel. The sensor is hydrated for this sensing contact by the presence of a fluid that is at least a hydrating fluid in the flow cell to maintain the one or more sensors in a hydrated state for ready-to-use application of the cartridge. In ionic contact with the sensor is a reference electrode in the reference electrode containment area of the flow cell. The reference electrode is in conductive contact with a contained quantity of reference electrolyte for the number of multiple sequential tests for which the cartridge is capable.

The electric circuit is attached for electrical conduction to the at least one sensor and at least one reference electrode. The circuit is located remote from and electrically isolated from the fluid in the channel of the flow cell. The circuit has the capability of conveying signals from the at least one sensor, and for providing any required electrical power to the electrodes in the flow cell. The electrical circuit is attached for electrical conduction to a signal conveyor which links the flow cell for electronic signaling to the exterior of the cartridge for electrical interface with the analyzer.

The flow cell can be in direct fluid communication with the reservoir through its second or any additional opening so that fluids leaving the flow cell flow to the reservoir. The directional flow control means is associated with the reservoir and/or flow cell so that fluid can be maintained to keep the sensor hydrated and to retard backflow of fluid from the reservoir.

The analyzer of the system is electrically connected to the signal conveyor of the cartridge along with an electronic means for interpreting these signals and a display for displaying the results of calculations to determine the amount of analyte in a fluid. The electronic means interprets the signal sent from the sensor for the calibrant and the multiple, sequentially-introduced samples having one or more analytes. This means also calculates the amount of the one or more analytes from these received signals. Additionally, the analyzer has an encoded information reader for imputing encoded information for calibration.

In addition, the system has external to the cartridge at least one container of calibration fluid which has a known amount of one or more analytes that are those analytes to be measured in the multiple samples introduced into the cartridge. Since the calibrating fluid is initially external to the cartridge, the calibrating fluid additionally is associated with an encoded information carrier having detailed information about the quantities of analytes in the calibrating fluid. Additionally, when the containers of calibration fluid are packaged with the cartridge, the encoded information carrier for the calibration fluid can have information about the one or more sensors in the flow cell and their associated premeasured sensitivities to analytes to be measured. Otherwise with the cartridge packaged separately from the calibration fluid, two encoded information carriers are used. One is for the calibration fluid and the other is for the sensor(s) in the cartridge having the respective aforementioned information for inputting into the analyzer through the information reader.

The method of using the system of the present invention involves a calibration fluid with associated encoded information carrier about the calibrating fluid. The encoded information is read into the analyzer's microcomputer or microprocessor through a reader. Also, through the same or different encoded information carrier, encoded information about the one or more sensors in the flow cell is inputted into the analyzer through the reader. The calibration fluid is injected or introduced into the inlet of the cartridge to calibrate the sensor(s) in the flow cell. The calibration fluid displaces the hydration fluid in the channel of the flow cell and the hydration fluid flows into the waste reservoir. The at least one sensor electrically responds to the presence of the amount of the one or more analytes in the calibration fluid and signals this response to the analyzer. The analyzer uses this information and the information from the encoded information of the at least one sensor. At this point, the sample with an unknown value of a known analyte is introduced into the inlet of the cartridge to flow into the flow cell to contact the one or more measuring sensors. This forces the calibrant out of the flow cell and into the waste reservoir. As with the calibration fluid, the sensor(s) respond and signal(s) are transmitted or conveyed to the analyzer. The analyzer interprets the signals and from the calibration information calculates the amount of the known analyte in the sample and displays it on the display means. Additionally, the analyzer can have a printer to print a hard copy of the analysis.

In this method the performance characteristics of the one or more measuring sensors can be inputted into the analyzer through the calibration fluid analysis and/or by means of inputting encoded information associated with the cartridge. This need only be done once for all of the multiple samples passed through the flow cell for a cartridge. When the cartridge is exhausted, it is disposed of and another cartridge can be connected electrically to the analyzer and the encoded information for this cartridge is inputted through the reader of the analyzer for additional testing of samples.

When the system is used for determining gas values in a liquid, the cartridge can be packaged in a gas impervious packaging material and the atmosphere within the bag can be controlled with a known gas atmosphere. The containers of calibration fluid may be packaged with the cartridge or in a separate package which may or may not be gas impervious. Additionally, gas impervious packaging may be used with a known gas atmosphere for containers of additional hydrating fluid or flush fluid for the sensors. The encoded information carrier for the cartridge and the calibrating fluid can be located on the exterior of the packaging material.

BRIEF DESCRIPTION OF THE DRAWINGS

FIG. 1 is an elevational view of the top of the cartridge attached to the analyzing means.

FIG. 2 is an orthogonal view of the top, front and side of the cartridge detached from the analyzer.

FIG. 3 is a side view of a package with a cut-away showing a side view along lines 3—3 of FIG. 1 of the cartridge inside the package.

FIG. 4 is a sectional view of the side of the cartridge taken along the lines 3—3 as is FIG. 3.

FIG. 5 is a sectional view of the cartridge from the opposite side from that of FIG. 4.

FIG. 6 is an elevational view along lines 6—6 of FIG. 4 showing the sensor housing and sensor therein. FIGS. 6A and 6b, 6c are sectional views transverse to the longitudinal axis of the flow cell.

FIG. 8 is plan view of the back of the analyzer along lines 7—7 of FIG. 1.

FIG. 9 is a plan view of the bottom of the analyzer.

DETAILED DESCRIPTION OF THE INVENTION

Figure 7:
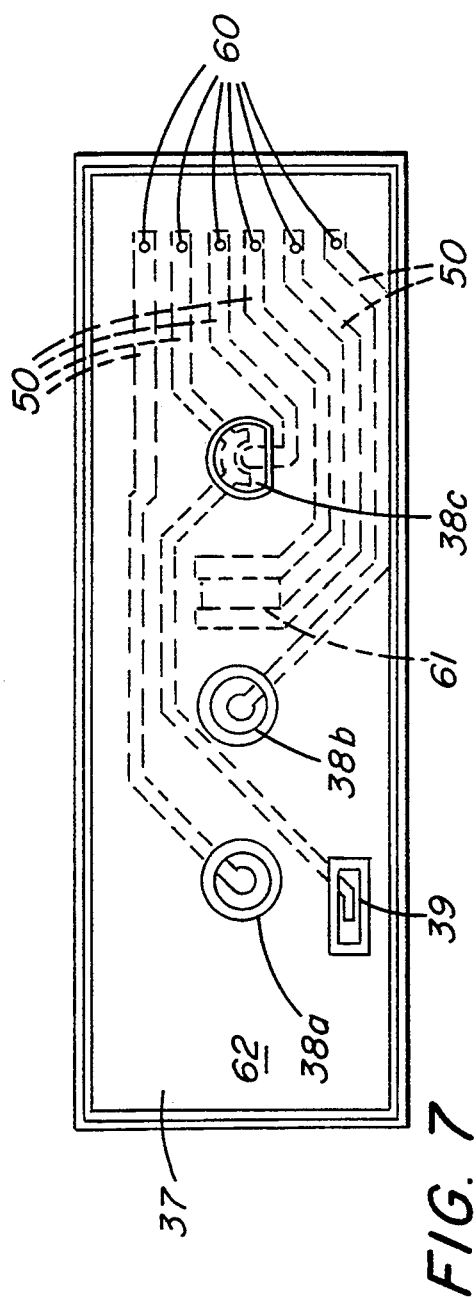
FIGS. 7 and 7a are elevational views of the electric circuit means and the sensors on the nonconducting substrate for the present invention.

The present invention is directed to a fluid analyte measuring device having a ready-to-use, multiple use sampling cartridge that is disposable. Samples can be injected directly into the cartridge without any special sample preparation or special holding devices so the system provides the advantage of direct introduction like stationary analyzing equipment. Additionally, the system with the multiple use disposable cartridge is, in fact, portable for ease of use and the cartridge is disposable to minimize contact with the samples. After disposal of one cartridge another can be used in the measuring device.

FIG. 1 shows the cartridge 11 and analyzer 12 of the multiple use analyte measuring device 10. The cartridge 11 is a multiple use disposable unit which is electrically connected to the analyzer 12 through electrical connection 13, which acts as a signal conveyor. The cartridge 11 as shown in FIG. 1 shows the inlet 14 for placement of chemical fluids for measurement, preferably through injection, at 14, which has an associated cap 15 which is removably attached thereto. In the cutaway of the cartridge in FIG. 1, there is shown the flow cell 16, which is supportively positioned within the cartridge housing having an inlet 14 at the end proximate to cap 15 and a flow control means 17 which can be a unidirectional valve at the distal end of the flow cell 16. Electrical connection 13 can be a prong connector or a cable as known to those skilled in the art. If the cartridge 11 is not mechanically attached to analyzer 12, the electrical connection 13 is a cable such as a ribbon cable for electronic communication between the flow cell 16 and the analyzer 12. In this manner, the analyte measuring device of the present invention is portable and has a sample receiving means, the cartridge 11, which is detachable from the analyzer 12 and is capable of a multitude of tests after which it is disposable.

The cartridge shown in FIG. 2 is detached from the analyzer 12 giving a clear view of the electrical connector 13 as a prong connector. The cartridge 11 can have any shape to serve as a housing for the flow cell with its one or more sensors. Hereinafter in the specification, the terms "one or more sensors" and "at least one sensor" will be referred to in the plural to include both the singular and the plural. The shape can be designed to match that of the analyzer 12 or could be a cube or rectangular box with a ribbon cable attachment as electrical connector 13 to the analyzer 12. The analyzer 12 shown in FIG. 2 has the slide-through encoded information reader 22, which is electrically connected as aforementioned to the microprocessor within the analyzer 12. On the exterior, the analyzer 12 has display area 27 for display of numerical values and functions performed by analyzer 12. Also, the analyzer 12 can have a printer for a hard copy display of information electrically displayed in display area 27. The printer 28 can be any printer known to those skilled in the art that is small and compact. The display area 27 can consist of any set of LCD displays or the like known to those skilled in the art arranged for a convenient display of numerical values and functions performed by the analyzer 12. The analyzer 12 also can have handle 29 to aid in its portability.

FIG. 3 shows cartridge 11 inside a gas impermeable bag 18 to maintain the flow cell 16 and tile sensor therein within a certain atmosphere 19. Cartridge 11 is shown in a side view along the lines 3—3 of FIGS. 1 and 2. The cartridge can have removable cap 15, which is preferably reusable, covering the inlet 14 in fluid engagement with the flow cell 16 having at its distal end the flow control means 17 like the unidirectional valve for fluid engagement with waste reservoir 20 as shown in FIGS. 4 and 5. Also, the cartridge 11 has an encoded information carrier 21 associated with it to carry information related to sensor values and information on any temperature sensor that can be present in the flow cell 16. The sensor values would include the performance characteristics including sensitivities of one or more of the electrodes for one or more of the analytes to be measured and different slopes for the function of the change in electronic values for changes in concentration of a particular analyte.

As shown in FIG. 3, the orientation of the flow cell is preferably a straight line orientation with the inlet 14 and the flow control means like one-way valve 17. Preferably, the orientation of the flow cell 16 is nonhorizontal with respect to the horizontal plane passing through the width axis of the cartridge 11. Preferably, flow cell 16 has this orientation because of the arrangement of the electrodes with their electrolyte in the flow cell, as more fully discussed for FIG. 6, and for good flow through the flow cell 16. The latter allows for facile flushing of a previous sample from the multiple use flow cell before measurement of a subsequent chemical sample. The orientation of the flow cell 16 within cartridge 11 can be even horizontal with appropriate modifications of the electrodes in flow cell 16. For instance, the reference electrolyte for the reference electrode could be a gelled electrolyte.

The encoded information carrier 21 can be any means for containing information that can be inputted into the analyzer 12. A few nonexclusive examples of encoded information carrier include bar codes, magnetic stripes, optical encoding, keyboarding, semiconductor electronic memory, electromechanical punch cards, and touch memory chips. The latter are stainless steel, self-stick labels that read or write with a momentary contact. The touch memory chip is packaged in a coin-shaped MicroCan holder to withstand harsh environments. The simple conductive surfaces of its package are conduit for error-free data transfer to other chips in the system in a direct chip to chip digital link. Preferably, the encoded information carrier 21 can be and is a bar code which contains information by having alternate elongated dark bars and light spaces to represent digital and alpha numeric codes. For example, the universal product code (UPC) is commonly used on retail products. The analyzer 12 has a reader 22 for encoded information. For instance, when the information has a bar code, the bar code 21 can be on the bag or foil wrapper 18 which is passed through the reader or the reader passed over the bar code. Additionally, the encoded information carrier can be a sticker on the cartridge 11 or any other means so long as the information for the sensor can be inputted into the analyzer 12.

A nonexclusive example of a bar code reader includes a wand having a light-emitting diode shining through an aperture at one end of the wand. The wand can be held vertical relative to the bar code label 21 and is passed directly from one end of the bar code label to the other. This is referred to as "scanning of the label". A photosensitive device, such as a photo-transistor, receives light that is emitted from the light-emitting diode and is reflected by the light spaces between the dark bars in the label. The wand typically includes a single stage amplifier that amplifies the output signal produced by the photo-sensitive device. The signal referred to as the wand signal or analog signal typically has an amplitude of roughly 200 to 300 millivolts. Where the reader 22 is a wand-type reader, these signals could be conducted by means of a flexible cable extending from the upper end of the wand. The signal would go to wand conditioning circuitry that further amplifies and shapes the wand signal to produce a raw data signal that includes a sequence of pulses and intervals therebetween with a constant scan velocity of the widths of the pulses and intervals accurately correspond to the widths of the bars and spaces. The signal produced by the wand conditioning circuitry is inputted into a microprocessor system to execute algorithms for converting the raw data signal into binary numbers with one such binary number corresponding to each character in the bar code and each bit having a logical state (either a 1 or a 0) that corresponds to the width of the bar or space of the bar code label. Once the binary numbers are obtained, the characters represented thereby automatically can be obtained by the microprocessor with reference to its data information bank. Any bar code, information source and method for decoding same known to those skilled in the art can be used. Preferably, the bar code reader 22 is a stationary attachment on the analyzer 12.

FIG. 4 shows a sectional view through cartridge 11, where the section is taken in front of flow cell 16. The cartridge preferably has a recess 23 for mechanical attachment to analyzer 12. Also, this view shows the inside of plug connector 13 for electrical attachment to the analyzer 12. The cap on inlet 14B is removable for multiple uses of the inlet. The inlet 14B here is a unidirectional valve and preferably the inlet is adapted to receive a needle or a front end Leur fitting section of a syringe with the needle removed for injection of a fluid, preferably blood, for analysis of the analytes, preferably blood gases. Inlet 14B can have a unidirection valve like a check valve to make the inlet unidirectional for flow into the flow cell 16. The flow cell 16 is in fluid communication with the inlet 14 and preferably is connected at its distal end to the flow control means 17 as a one-way valve. Valve 17 can have conduit 24 for direct connection with a waste reservoir 20.

FIG. 5 is a sectional view of the other side of cartridge 11 from the side depicted in FIG. 4 so that the flow cell 16 is shown in FIG. 5 from a sectional view of FIG. 3. The cartridge 11 has waste reservoir 20 which is preferably a biax nylon laminated to clear polyethylene bag having a continuous inner and outer seal. Preferably, the bag is double-edged and is bulk packed in cartridge 11 to be expandable. The cartridge housing can have at least one vent for atmospheric gases. Looking through the clear bag 20, the reservoir port 26 is in view which is in fluid connection with conduit 24 to receive fluid from flow cell 16 through flow control means 17. Preferably, 17 is a one-way or unidirectional valve like a check valve, but the flow control means can be any other device known to those skilled in the art to retard backflow. Preferably, the flow control means also provides for maintenance of some fluid in the sensor housing to keep the sensors hydrated.

FIG. 6 is a top plan view of the flow cell 16 taken along line 6—6 of FIG. 4, showing the general arrangement with the sensor assembly where the channel can contain fluid. The flow cell housing 35 is made of any fairly rigid moldable material such as rigid thermoplastic polymers although thermosetting polymers can also be used. A suitable example is a methyl methacrylate styrene butadiene terpolymer and rigid plastics such as polyesters like polyethyleneterephthlate or polycarbonate or blends or alloys thereof and other similar materials known to those skilled in the art. The housing 35 can be any basic geometric shape suitable for containing channel 36 and sensor element 37. The number of parts comprising the housing 35 can range from 1 to a plurality, but two parts are preferred. A single part housing is at least that which provides a suitable channel 36 for fluid communication with the one or more sensors 38 on sensor element 37. In this arrangement the sensor element 37 can actually form one side of the housing 35. The housing 35 also supplies an opening for an electrical connector 13 for electric attachment to the electrical circuit 50, as shown in FIGS. 7, for sensor element 37. The sensor element 37 has sensors 38 with a hydrophilic membrane where part of the sensors are electrically connected to an electric circuit means 50 and both the sensor 38 and electric circuit means 50 are on a nonconducting substrate of sensor element 37 that is in the flow cell 16 in the sensor containment area 42. The sensor 38 is located on element 37 and channel 36 and element 37 are arranged in housing 35 in a manner so that sensor 38 and channel 36 can be in fluid contact with each other when channel 36 is filled with a hydrating fluid 34.

Housing 35 has at least one and preferably two openings, 40 and 41, arranged along channel 36 at different locations from each other in relation to sensor element 37. This arrangement allows fluids introduced at inlet 14 to flow from fluid pressure through opening 40 at inlet 14A of the flow cell and into channel 36 for contact the sensors 38 on sensor element 37. Channel 36 can have any shape that allows for laminar flow of fluid through it in the vicinity of the sensors 38 in the sensor containment area 42 along channel 36. Also, the openings 40 and 41 are in fluid communication with inlet 14 and one-way valve 17, respectively. As aforementioned, opening 40 can serve as an inlet to housing 35, and 40 is preferably formed by conical tip 44. Also, the housing at the other end of the sensor element 37 from opening 40 can have a flared end (not shown in FIG. 6) that would encompass opening 41 that is formed by tip section 45, which preferably has a cylindrical exterior and a conical interior. The tips 44 and 45 are preferably aligned in the same plane and along the same axis at opposite ends of the channel 36 so channel 36 passes longitudinally through the housing 35 along the same central axis. This arrangement provides sufficient support of channel 36 by housing 35 to receive and/or expel fluid into, through and out of channel 36 with application of fluid pressure to the channel 36 of the flow cell. Preferably, the shape of tips 44 and 45 are of a standard outer diameter to allow for connection to the inlet 14 and the one-way valve 17 directly or by tubing or conduits.

Housing 35 preferably has one section 46 and another section 47 which have matched attachment means (not shown in FIG. 6 but shown in subsequent Figures) for connection to each other. Sections 46 and 47 fixedly engage to form the housing 35 having one or more internal spaces as containment areas (a portion of which is shown in FIGS. 6a, 6b and 6c as 42) for placement of sensor element 37. FIGS. 6a and 6b are sectional views through the flow cell. The internal space as sensor containment area 42 need not be of any particular geometric configuration just so long as sensor element 37 fits into the space. The containment area 42 and sensor element 37 are preferably of matched configuration and are preferably generally rectangular. Preferably, one section 46 comprises a substantial portion of housing 35 as shown in FIG. 6a and the other section 47 is a cover for the back of sensor element 37 occupying internal space 42 of FIG. 6a. With this arrangement and with the containment area 42 having dimensions that closely match those of the sensor element 37 for a snug fit of the latter into the former, the sections 46 and 47 can assist in providing electrical isolation between the hydrating fluid 34 and the electric circuit means 50. The former is at least in channel 36 and the latter is on sensor element 37. Also, the flow cell 16 has at least one reference electrode 39 which is in the reference containment area 43 formed from the sensor element 37 and the flow cell housing section 46. Reference electrolyte 49 that is also present in the reference containment area 43 contacts the reference electrode 39. Preferably, the reference electrode containment area 43 intersects with channel 36 for conductive fluid contact of the reference electrolyte 49 and the hydrating fluid 34 or sample fluid in channel 36. This arrangement forms a liquid junction with the sensors contacting the channel 36. Preferably, section 46 has the tip sections 44 and 45 and has any flared ends and forms a portion of channel 36 and any other channels that are present. The remaining portions of the channel 36 or other channels are formed by sensor element 37 occupying the containment area 42 so that the surface with sensors as 38 actually forms a wall of the channel 36 as shown in FIG. 6a. Any arrangement or configuration other than that shown in FIG. 6a can be used that allows the two sections 46 and 47 to engage and form housing 35 with one or more internal spaces as containment area for placement of sensor element 37 so that the one or more sensor 38 is in fluid contact with hydrating fluid 34 that is in channel 36.

The sectional elevational view of the sensor apparatus shown in FIGS. 6a, 6b, and 6c are along lines 6—6 of FIG. 6. As shown in FIG. 6a on housing 35, ridges 53 and 54 can be present for ease of handling. The electrical connector 13 is shown as a cable extending from the bottom of housing 35. These views show the preferred embodiment of the invention having a plurality of channels. The one channel is channel 36 for the flow of fluids through the flow cell, and the additional channel or channels are for the reference electrode containment area 43. Preferably, this area is formed by one additional channel for each reference electrode. Preferably, there are two reference electrodes in spaced apart relation to each other so there are two channels, 51 and 52.

The containment space 43 has the at least one reference electrode 39 and its reference electrolyte 49 in fluid contact therewith. Preferably, the reference electrolyte is hydrating fluid 34. As shown in FIGS. 6, 6a, and 6b, channel 36 is in fluid contact with sensors 38 which are on sensor element 37. Also shown in fluid contact with channels 51 and 52, respectively, are reference electrodes 39 and 39a. The reference electrode can be any reference electrode known to those skilled in the art, but preferably it is a bare wire or tracing of the electric circuit 50. The reference electrode containment area 43 has sufficient electrolyte to be effective for the number of tests in the multiple test unit. Preferably, the area 43 is in liquid junction communication with channel 36. The geometric design of the area 43 can be any design that keeps the electrolyte 49 in contact with the one or more reference electrodes 39 during the number of multiple use tests, which can range from more than 1 up to around 75 or more separate tests. For instance, the design can be one that allows for use of the flow cell in any orientation in the cartridge 11 when the electrolyte is a gel. When the design of the area is as shown in FIGS. 6, 6a, and 6b, it is preferred that the flow cell 16 is oriented in cartridge 11 in a nonhorizontal manner in respect to the horizontal plane through the width axis of the cartridge 11. Hence, the flow cell can have an angle that is an acute or obtuse angle in respect to this plane, when the design of the area 43 involves a channel for each reference electrode that are coplanar with channel 36. Preferably, this or these reference channels run parallel to channel 36 and intersect with channel 36 at the proximate end of the flow cell 16 relative to the inlet 14.

The hydrating fluid 34 is any liquid suitable for maintaining the membrane of sensors 38 in a nondried state. For instance, the liquid will have some amount of water although a minor quantity of organic liquids may also be present. Preferably, the liquid is a stable liquid for storage ranging from a short time (days or weeks) to prolonged periods of time of several months. Preferably, the liquid is an aqueous solution that is isotonic with any electrolyte in the sensors. More preferably, the hydrating fluid 34 is also isotonic to act as the electrolyte for any reference electrodes that may be present on the sensor element 37 as reference electrodes 39 and 39a as shown in FIGS. 6, 6a, and 6b. A suitable example of a hydrating fluid is an aqueous solution comprising: disodium hydrogen phosphate, potassium dihydrogen phosphate, sodium bicarbonate, and sodium chloride. Such a solution can have a varying range of amounts for the individual constituents but most preferably, for the aforelisted salts, the amounts are in millimoles per kilogram of water in the order listed as follows: 4.8, 13, 22 and 12.5. The quantity of hydrating fluid in channel 36 or the plurality of channels including the reference electrode containment area 43 is at least that which is sufficient to cover or remain in contact with the sensors. Also when this fluid is used as the reference electrolyte, the amount is also sufficient to provide a liquid junction between the one or more reference electrodes and the sensors.

Also as shown in FIG. 6a and 6b, there may be and preferably are present two longitudinal slots 55 and 56 which are in the top section 46 of housing 35. These slots are for mold enhancements for plastic molding of the housing 35 to assist in obtaining flat external and internal surfaces for a larger housing section. Housing section 46 securely fastens to housing section 47 by matching fastener 57 on top section 46 and 58 on bottom section 47. Any other fastening means known to those skilled in the art can be used. Mirror image fastening means are present on the opposite side of housing 35.

The housing 35 can have, and preferably does have, a plurality of attachment ports 59 to assist in holding the sensor element 37 in place in the sensor element containment space 42 and to assist in attachment between section 46 and section 47. The preferred rectangular shape of sensor space 42 is shown in FIGS. 6(a) and 6(b). The number of ports can range from around 2 to around 8 although higher numbers can be present and the ports can range in geometric configuration from circles to slots to square and the like for mechanical or chemical attachments. The mechanical attachments can be plastic or metal rivets or fasteners like screws and the chemical attachment can be adhesives, preferably curing adhesives such as a UV-curing adhesive. FIG. 6 shows eight ports (59A–59H). The arrangement of the ports are sufficient to accomplish positioning and holding the sensor element 37 in space 42.

Preferably, as shown in FIGS. 6A and 6b, an electrical insulator 48 is present. The electrical insulator 48 can be any material that can occupy spaces between housing sections 46 and 47 and sensor element 37 other than the one or more channels and electrical connector 13 to assist in providing for electrical isolation. The insulation can restrict any contact between any hydrating fluid 34 and the electric circuit 50 to reduce the possibility of any short circuits or leakage current. This material preferably has the following characteristics: an insulation factor of around $10^{14}$ ohms/cm$^2$ and substantially impervious to moisture and preferably curable at a temperature of less than around 60 degrees Centigrade. Nonexclusive examples of a suitable material include: epoxy polymer, modified epoxy molding compound such as brominated epoxies, epoxy molding compounds, polyimides, unmodified polylmides like PMDA-ODA and BTDA ODA-based polyimides, Poly(amide-imide) polymers, modified polyimides having modification from diamic acid additives, siloxane polyimides, and high temperature polymers like silicone polymers, and polyarylene ether polymers. A particularly suitable material is a bisphenol A epichlorohydrin type epoxy polymer like that available from the Hysol Division of The Dexter Corporation in Industry, California 91749 under the trade designation EE4207.

Figure 7A:
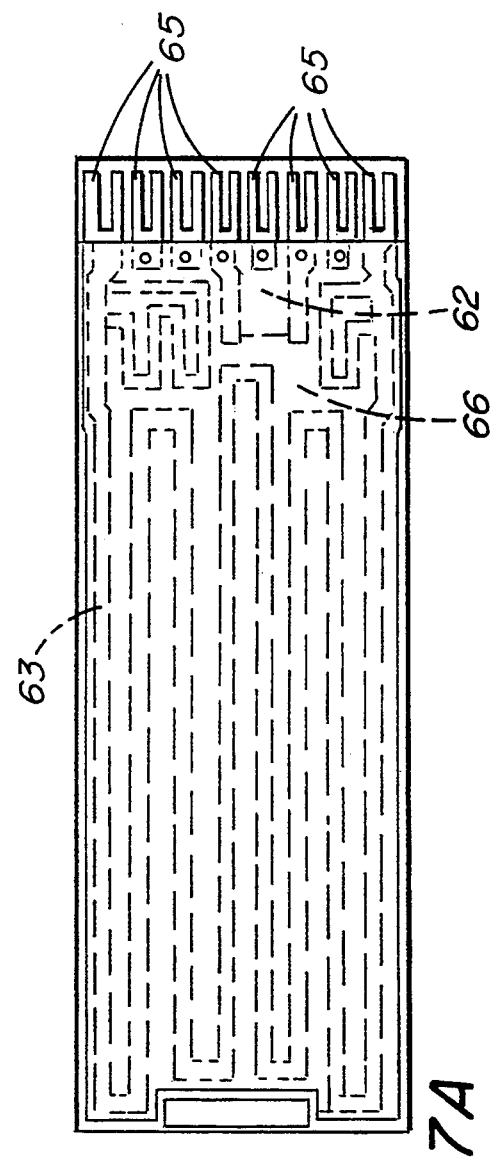

In FIGS. 7 and 7a, the sensor element 37 can have sensors like sensors 38 a-c having one or more hydratable membranes which can be any such sensors and membranes known to those skilled in the art. For instance the sensors can be potentiometric or amperometeric like 38 (a) and (b) and 38 (c), respectively, and at least one reference electrode 39 is present. Preferably, sensor element 37 is a nonconducting substrate with an electrical circuit 50 electrically connected to sensors through at least one electrode. Generally, the nonconducting substrate can be a glass or ceramic including sheet or chip or nonconducting substrate like nonconducting polymers or commercially available frit that can be used as the substantially smooth flat surface for the nonconducting substrate. Nonexclusive examples include borosilicate glass as is known to those skilled in the art for producing thick film or layered circuits. A nonexclusive but preferred example of which includes a ceramic base having around 96% A1203 such as that available commercially from Coors Ceramic Company, Grand Junction, Colo. Generally, the electric circuit 20 is any electrical circuit means known by those skilled in the art. Both the sensors 38 and the electric circuit 50 can be prepared from any number of well known layered circuit or integrated circuit technologies, as for example, thick film, thin film, plating, pressurized laminating and photolithographic etching, and the like, however, the thick film technique is preferred. A suitable sensor element is that described in U.S. Pat. No. 5,046,496, issued Sep. 10, 1991, entitled "Sensor Assembly for Measuring Analytes in Fluids", which is commonly assigned. The sensors 38 can be from thick film, thin film, fiber optic, and coated wire types of sensors that can be potentiometric or amperometric sensors, in that the former has one electrode and the latter has two, both an anode and a cathode. Preferably, the sensors are thick film sensors and include two potentiometric sensors and one amperometric sensor when the flow cell 16 and cartridge 11 are used to measure blood gases. The potentiometric or amperometric sensor preferably has a hydrophilic polymeric membrane and the sensor preferably has an aqueous-based electrolyte with suitable ionized chemical species like those in silver/silver chloride, calomel and mercury sensors or electrodes. Suitable examples of such membranes that may be present in electrochemical sensors for use in determination of blood gases are described in U.S. Pats. Nos. 3,088,905; 3,912,614; 4,133,735; and 4,454,007 and European patent specifications 0015075 and 0027385 and the article in the journal entitled "Medical and Biological Engineering Computing", 1978, Vol. 16, pages 599–600. The publications describe blood gas detectors requiring the presence of membranes and a number of useful or potentially useful membrane materials. Suitable nonexclusive examples of a hydrophilic polymeric membrane include polyvinylchloride and modified polyvinylchloride and any similar hydrophilic hydratable polymeric membrane known to those skilled in the art.

The electric circuit 50 is shown in FIGS. 7 and 7a, to optionally, but preferably, include a temperature detector 61 and accompanying resistor 62 and a heater 63. These Can be any such components known to those skilled in the art. The connectors 60 allow for a conductive path in the electric circuit 50 to the second surface of the board 66. The cable connectors 65 allow for the connection of the electric circuit means 50 to electrical connector 13 preferably by a prong connector 13 as shown in FIG. 2. The prong connector permits electrical connection from the nonconducting substrate of sensor element 37 in the interior of the cartridge 11 to the exterior of the cartridge 11 to the analyzer 12. Alternatively electrical connector 13 can be any suitable electronic multiple conductor with suitable leads to carry analog signals and preferably not binary signals. Preferably, the cable is a ribbon-type cable with a plurality of wires in one tape-like strip to provide the sensor element with electrical communication from the sensors. The connection of the electrical circuit means 13 to the nonconducting substrate of 66 is in a manner to communicate electrically with at least the sensors or electrodes but to avoid contacting the hydrating fluid 34 which may cause short circuits or current leakage.

The flow cell 16 is prepared by placing the sensor element 37 with sensors 38 having unhydrated membranes, preferably three sensors, one for measuring the partial pressure of oxygen, another for measuring the partial pressure of carbon dioxide and a third for measuring the pH of fluids, preferably fluids like blood. The sensor element 37 is placed in the containment area 42 of flow cell member 46 as shown in FIGS. 6, 6a, and 6b. The electrical connector 13 is electrically connected to sensor element 37. When the sensor element 37 is placed in containment area 42, this electrical connection is preferably at the distal end although it could be at the proximate end of housing 35. The cable stretches along the length of the sensor element 37 between the element 37 and the housing member 47 and exits housing 35 at the near proximate or exiting end 67. Additionally, it is preferred to have a foam pad between the electrical connector 13 and housing member 47 so that there is uniform compression of sensor element 37 to the bottom of housing section or member 46. Housing members 46 and 47 are aligned and preferably snapped together through the pair of fasteners 57 and 58 as shown in FIG. 6b.

An adhesive that is curable by ultraviolet light is placed in at least some of the ports 59a through 59h and also preferably along the interior surface of the housing member 46 by wicking. Any suitable adhesive known to those skilled in the art of joining polymeric parts to glass or ceramic substrates can be used, but it is preferred to use an ultraviolet light curable adhesive that is substantially water insoluble in the cured state. A nonexclusive example of a suitable material is the UV curable epoxy adhesive available from electronic materials vendors. Also this adhesive may be used with about 0.005 percent by weight polychrome blue organic dye to highlight the details of the adhesive. Before placing the housing with the adhesive in a UV-curing zone to cure the adhesive, it is preferred to allow the adhesive to wick within the sensor element containment space 42 along the surface of housing member 46. The wicking of the adhesive within the cavity is preferably on both sides of the reference electrode channels 51 and 52. Preferably, the quantity of adhesive that is used allows for wicking lengthwise along the bottom of section 46 on both sides of channel 36 and under the channel so the bead of adhesive is near continuous on both sides of the channel 36. The curing can occur in any commercially available UV-curing oven with or without a conveyor. After curing the wicked adhesive, the housing 35 is cooled to ambient temperature. Preferably, now the UV-adhesive cured by ultraviolet light is placed in the ports and again placed in the UV-curing oven.

After the joining of the housing members with the adhesive, the electric insulator for electric isolation 48, preferably an epoxy, that is cured at room temperature and atmospheric pressure is filled through hole 68 in member 47 as shown in FIG. 6c into the internal space 42 that is not already occupied. To increase the rate of cure, the housing is preferably placed and maintained in an oven for about two hours at 60° C. After the electronic isolating material 48 has hardened or cured, as in the case of an epoxy material, the housing 35 can be pressure tested at an air pressure of around 10 to around 15 psi.

Upon joining of the housing members to contain the sensor element 37 and cable 13, one opening of the channel 36 is coupled with inlet 14 or one-way check valve 17 and the hydrating fluid 34 is added to channel 36 and the reference containment area 43 to fill substantially all of the channels although small amounts of air bubbles can be tolerated in the channels but preferably the channels are filled to capacity. The remaining opening of channel 36 is coupled to a second opening of the channel or the inlet 14 or one-way check valve 17 which was not previously connected and the flow cell is ready for positioning in cartridge 11 with the waste reservoir 20.

FIG. 8 is a view of the back of the cartridge 11 and analyzing means 12 in a view that is a 180 degree rotation about the elevational axis of the device shown in FIG. 1. This view shows the cartridge housing 11 having a raised area 30 which encompasses the inlet 1& that is attached to flow cell 16. The printer 28 is shown also in FIG. 8 and area 32 is a battery supply and AC connection. It is preferred that the unit have both a DC supply and an AC connection although it is possible that the unit have just one or the other.

FIG. 9 is the bottom of the analyzer 12 with attached cartridge 11 of FIG. 1 flipped 180 degrees about the longitudinal axis. This view shows the mechanical attachment 33 which forms a base plate of the cartridge 11 and analyzer 12. The mechanical fastener 33 of the analyzer 12 engages cartridge 11 through recess 23. The mechanical fastener can be any protruding element capable of attaching to and supporting a box-like cartridge which can develop a not inconsiderable weight when the waste reservoir is full of fluid. Also shown in FIG. 9 is the bottom of the printer 28, the handle 29 and the battery or power section 32. When the cartridge 11 has a full waste reservoir, the cartridge is removed from the mechanical fastener 33 of the analyzer 12 and discarded and a new cartridge is slidably engaged with mechanical fastener 33 through recess 23 of the cartridge 11 to provide additional tests.

In the aforedescribed sections of the device of the present invention, the arrangement of the components preferably result in sensors for measuring the partial pressure of oxygen and electrodes or sensors for measuring the partial pressure of carbon dioxide and for measuring pH are in channel 36, while channels 51 and 52 each have a reference electrode 39 and 39a, respectively. When hydrating fluid 34 is in the channels, the fluid in channel 36 is more easily displaced with the introduction through inlet 14 of sample fluid to be measured relative to the fluid 34 in channels 51 and 52. Therefore, reference electrodes 39 and 39(a) are measuring as a reference a known fluid for comparison for the measurement of the sample fluid in channel 36.

Figure 10A:
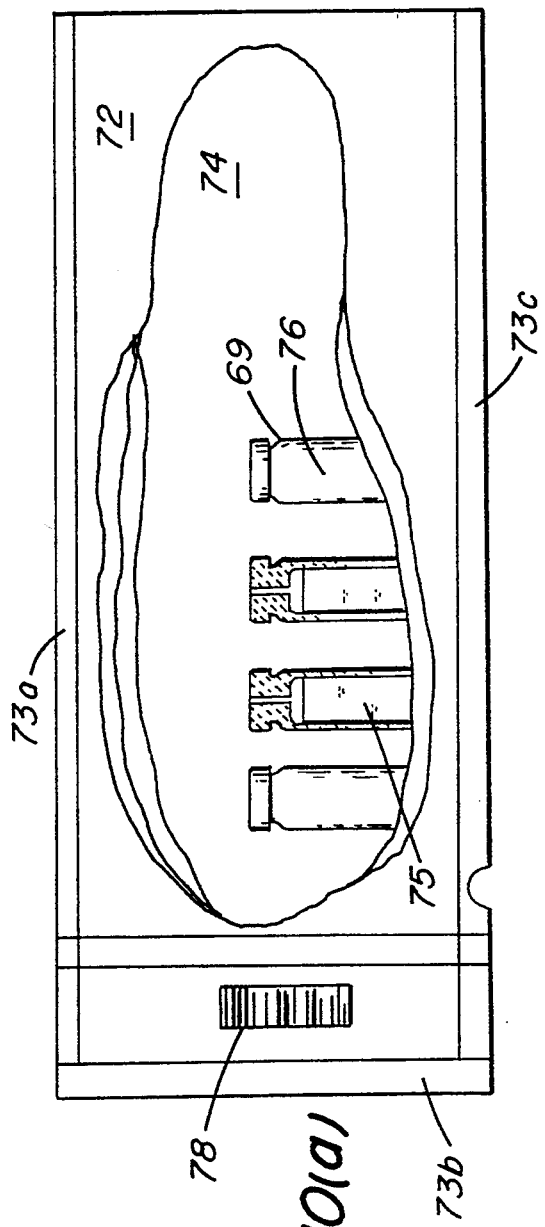
FIGS. 10a and 10b are elevational views of the packages of the calibration means, where for FIG. 10a the package has vials of fluids, and where for FIG. numeral 10b the package has fluids in delivery assemblies.

FIGS. 10 shows a package of vials or containers 69 and FIG. 10a shows a package of vials or containers 69 and delivery devices 70 and 71. When the analytes to be measured are gases like blood gases, it is preferred that the containers are in some way gas-tight. If the vial is gas impervious, the package does not have to be gas impervious. There are two situations where the package or wrapper is gas impervious. One is where the calibrating fluid or hydrating fluid is used as a flush between samples and the wrapper 72 is gas impervious to provide an atmosphere in the bag to equilibrate with the flush fluid. Another situation is where immediate containers for the calibrating fluid and/or flush fluid are not gas impervious. Wrapper 72 in FIGS. 10 and 10a can be the same type of material as that for bag 18 in FIG. 3. In both of these situations, the package 72 or bag 18, respectively, is a hermetically sealable layer that is preferably gas impermeable and diffusion tight and can be any single layer or multiple layer laminate type material that has these characteristics. Suitable multilayer material for these layers and for that of FIG. 3 includes metal foil polymer laminate material that can be heat-sealed to form a bag. The laminate material ordinarily has the interior layer of polymeric material and outside this layer a metal foil layer. The thickness of the inner polymeric or plastic layer is generally in the range of about 20 to around 80 microns. A typical laminate can have two or more layers but preferably has an additional outer polymeric layer to facilitate abrasion resistance or printing on top of the metal foil layer. A nonexclusive example of the metal foil is aluminum.

The three layer laminate suitable for the layer for a gas impervious wrapper or bag of FIGS. 3, 10 and 10a can have from the exterior surface to the interior layer the following: 1) nylon, polyester polyethylene or polypropylene, for example, 10 to 70 grams per meter$^2$ thickness for abrasion resistance; 2) aluminum foil, for example, 5 to 40 grams per meter$^2$ thickness; and 3) an inner heat sealable polymeric layer such as polyethylene, polypropylene, polyvinylidene chloride or nylon, i.e., of 5 to 25 grams per meter$^2$ thickness. A nylon-foil-polypropylene laminate of, i.e. 17 grams per meter$^2$ nylon, 32 grams per meter$^2$; aluminum, 45 grams per meter$^2$; polypropylene available under the trade name Sterilite NFP is suitable.

Another suitable example is a laminate having as an outer layer polyvinyl alcohol in an inner layer of a heat sealable polymeric material such as polyethylene, polypropylene, high-density polyethylene, polyester, a laminate consisting of nonstretch polypropylene and biaxially stretched polypropylene and an inner layer of nonstretch polypropylene and nylon as an intermediate layer and biaxially stretched polypropylene as an outer layer. Any of these heat-sealable polymeric films can be used as the inner layer with the polyvinyl alcohol. The hydroxyl groups of the polyvinyl alcohol are bonded with each other through hydrogen bonding providing polyvinyl alcohol with an extremely high impermeability (barrier property) to oxygen gas. The inner layer of the heat sealable polymeric film improves the heat sealability of the polyvinyl alcohol laminate. In addition, to retard deleterious effects of moisture or water in the environment on the polyvinyl alcohol layer, the exterior layer over the polyvinyl alcohol layer is a third polymeric layer. Suitable examples for this layer include biaxially stretched polypropylene, polyester, biaxially stretched nylon and polyvinylidene chloride film. A suitable laminate layer of this type is available commercially under the trade designation EVAR from Kuraray, Ltd.

A still further example of a suitable example is a polyfoil-polylaminate which is a three-layer composite having an aluminum foil intermediate layer and an inner and outer layer of polypropylene. In the metal foil laminate layer, the thickness of the aluminum foil is generally in the range of at least 20 microns to about 30 microns. The inner polymeric layer can also be selected from low permeable thermoplast available from ICI Chemicals, polyvinylidene chloride available under the trade designation SARAN, polyacrylonitrile-copolyme available under the trade designation PANG and BARAX 210; polyethylene terephthalate available under the trade designation MYLAR, polyvinylfluoride available under the trade designation PVF and polyamide-6 available under the trade designation NYLON-6 and polyvinyl chloride. The PANG is available from Lonzag, 4002 Basel and is described as a copolymer of a high proportion of acrylonitrile about 72 percent by weight and a low portion of other monomers, that is thermoelastically workable up to a temperature of about 150° C.

A bag of the layer is formed by any method known to those skilled in the art such as heat sealing. The size of the bag formed by the layer 72 will vary depending on the contents thereof and preferably can range from a size of about 4×7 cm to 6×10 cm to larger dimensions when additional components are included in the bag to include the cartridge 11 and possibly the addition of vials of calibrating fluid. In such a case the bag 18 can be from 6 to 25 cm wide to 10×40 cm long and can include a tear strip or tearing notch or line of weakness or the like expedient to facilitate opening. The seals can be placed along each end of the layer folded on itself or for two layers facing each other with their heat sealable polymeric layers, the inner layer of each edge can be sealed. Heat seals for the material folded on itself would be along two edges and one folded side like 73a, 73b and 73c of FIG. 10a. For two pieces of material facing each other, three heat seals would be made—one at each end like 73a through 73c. Typically, the heat seals 73a through 73c can be 9 to 10 mm wide. The heat seals are applied to the layer to allow for one open end of the bag. After the components are added to the bag, and any purging and atmosphere introduction is performed the opening is heat sealed in the same manner as the other sides.

In this description and in the accompanying claims, the term "equilibrating" is used in its art-recognized sense to mean that the gas and the buffer solution are maintained in contact with each other until such time as a state of equilibrium has been reached between the analyte in the controlled-content fluid and the analyte in the activating fluid.

The term "active state" for the sensor refers to the condition of the sensor that it is ready to detect analyte although calibration may be needed with conventional reference fluids.

"Preconditioned state" of the sensor refers to providing a sensor that is either in its active state and/or is in a diagnostic state, and/or is in a pseudo- or precalibration state and/or is in a calibrated state. The diagnostic state is that where the sensitivity of the sensor can be tested initially on first using the sensor with a display device not shown in the drawings. With this diagnostic information, the sensor can be tested for its ability to function prior to using it in analysis equipment. The pseudo or precalibration state is when the output from a calibrant or reference sample with a predetermined amount of analyte is compared with an output reading on a subsequent calibration or reference sample and a particular range of the change in values is expected for good operability of the sensor. Calibrated state is when the sensor initially gives an output reading on display equipment of some value or values for a calibrant or reference sample with a predetermined amount of one or more analytes.

For FIG. 3 the atmosphere 19 in bag 18 and for FIGS. 10 and 10a, the atmosphere 74 can be and preferably is a controlled-content fluid. For FIG. 3 the fluid or atmosphere 19 assists in maintaining the sensors 38 in an active state. For example, a sensor may have a water vapor permeable polymeric membrane like a hydratable polymeric membrane with some portion of its electrolyte that is aqueous. In this situation, the sensor needs to be maintained in a hydrating fluid to be active. Some sensors with hydratable membranes may be stored dry but they need the hydration of their membranes for the existence of an active state. For FIGS. 10 and 10a, the atmosphere 74 mimics the concentration of the one or more analytes in the calibrating fluid 75 or the flush solution 76 in nongas impervious containers.

The controlled-content fluid 19 contacts the cartridge 11 with the sensors 38 in flow cell 16 by the fluid's sealed presence within the bag 18. In this manner the controlled-content fluid 19 is between the gas impervious, diffusion tight layer and the sensors 38 by its presence within the bag 18 in fluid contact with the sensors 38 through plastic containers such as the cartridge 11 and the flow cell 16. The controlled-content fluid equilibrates with the sensors 38 that are in an active state in the presence of the hydrating fluid 3& in the flow cell 16 in order to precondition an active sensor.

In a similar manner in wrapper 72, the controlled-content fluid 74 is in contact with the hydrating or flush fluid 72 or a calibrating fluid 75 in gas permeable containers 76. Preferably, the calibrating fluid 75 is in gas impervious containers like the sealed vials 69 or glass ampules. Vials 69 can be glass vials with an opening that is heat-sealed with by a gas impervious material like those used for the bag 18. Preferably, the opening has the smallest practical diameter that allows for intentional ingress and egress of the fluid.

The controlled-content fluid can be a gas, liquid or combination of a gas and liquid depending on the state of the analyte that is detected by the sensor. Nonexclusive examples of such a fluid used as the atmosphere in the bag 18 and layer 74 are: normal air, moist air or air with a relative humidity greater than around 30 percent, or super-saturated moist air, or any similar moisture-containing or moisture-ladened inert gas. For a nonexclusive example, when the analyte is a blood gas such as oxygen and/or carbon dioxide, the controlled-content fluid 19 is a gas. One or more of these gases, oxygen and carbon dioxide alone or in combination with each other or with inert gases can purge the bag 18 after the cartridge 11 with the flow cell 16 having the hydrated sensors 38 is placed in the bag 18 and prior to hermetic sealing. Also, it is possible that the controlled-content fluid 19 is just the inert gas when it may be desired to provide a zero quantity of the analyte in the fluid.

The calibrating fluid 75 in vial 69 is a fluid containing a known set amount of the one or more analytes to be measured. When the calibrating fluid 75 is a combination of gas and a liquid, such a fluid can be produced with the requisite quantity of the gas by any method known to those skilled in the art. For example, such a fluid can be a tonometered fluid produced by any of the commercially available tonometers like the one available from Instrumentation Laboratory under the designation IL237 or by any method known to those skilled in the art like the techniques shown in preparing tonometered buffered solution or whole blood described in the article entitled "Quality Control in Blood pH and Gas Analysis by Use of a Tonometered Bicarbonate Solution and Duplicate Blood Analysis in Clinical Chemistry", Vol. 27, No. 10, 1981, pages 1761–1763, the description of which is hereby incorporated by reference. For such fluids the liquid can be an aqueous solution that is buffered and contains oxygen and carbon dioxide for use in blood gas measurements. Such solutions can be prepared in accordance with U.S. Pat. No. 3,681,255.

An example of an equilibrated or tonometered fluid as fluid 75 can result from contact of the buffered liquid solution with the carbon dioxide containing gas which can include a mixture of carbon dioxide with one or more inert gases. An inert gas is one which does not react with the buffer solution. This potentially would destroy the predictability of final calibrating fluid. Also, inert gas is one that does not react with any of the ingredients in the fluid to which it is added. Nonexclusive examples of inert gases are nitrogen, argon and other similar gases normally found in the air. This includes the noble gases such as neon, argon, krypton, xenon, helium and the like. It is preferred to use as the equilibrating gases for blood gas analysis a mixture of carbon dioxide and nitrogen or carbon dioxide with oxygen and nitrogen. Two nonexclusive examples include: 1) around 5 percent carbon dioxide with nitrogen making up the balance of the gas in the fluid and 2) around 7 volume percent carbon dioxide and around 10 volume percent oxygen and the balance is nitrogen.

The controlled-content fluid 19 and 74 with the controlled amount of gas or equilibrated with gas is maintained in an environment which prevents the diffusion of gas or vapor into or out of the system to prevent any drifting of the partial pressure values and any change in pH value. Art-recognized apparatus for maintaining this fluid can be used and one such example is the aforementioned commercial tonometer.

The cartridge 11 with the flow cell 16 with the sealed hydrating or activating fluid 34 in fluid contact with the Sensors 38 is placed in the layer bag 18 and the last unsealed edge or all of the edges are sealed at this time. The manner of sealing can be the heat or induction sealing methods as aforementioned for the seals to the housing except with the use of a different attachment to fit over the edges to make the seal.

Figure 10B:
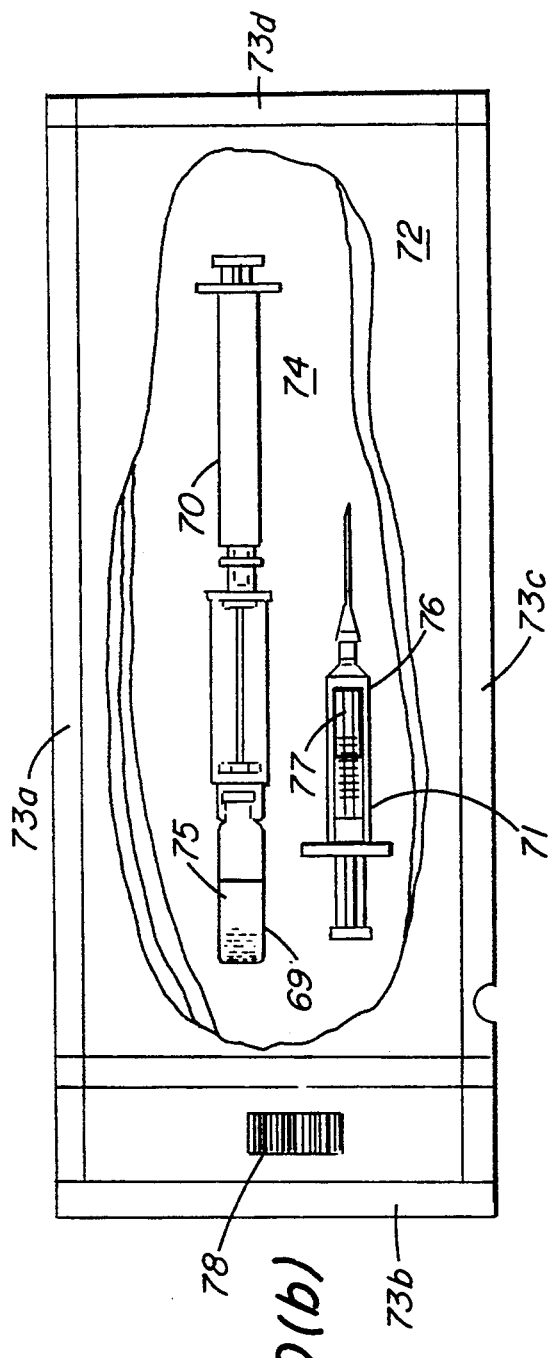

FIGS. 10 and 10a show the calibrating fluid 75 and flushing fluid 77 in packages 72 with the encoded information carrier 78. FIG. 10b shows the calibrant and flushing solution with the encoded information carrier 78 of the preferred embodiment of the present invention where there is also present a calibrant delivery device 70 and a flushing fluid delivery device 71. Most preferably, carrier 78 like carrier 21 is affiliated with the package 72 in a user friendly fashion. Carrier 78 can be of a similar type as that of carrier 21 and contains information about the concentrations of the analytes in the calibrating fluid.

The bag or envelope 72 of FIGS. 10 and 10a is purged with the controlled-content fluid 74 or a gas in a similar manner to that previously described With this addition the envelope 72 is sealed by heat or induction sealing at the last remaining edge so that the previously sealed edges of the layer 70 provide an envelope or bag to hold the controlled-content fluid 74. The sealing is accomplished in a manner similar to the envelopes for FIGS. 3.

Generally, the heat sealing is conducted for a time sufficient to perform melting and bonding of the sealable resin, for example 0.1 to 5 seconds. The heat sealing operation can be performed in an operation comprised of one stage or two or more stages. In the latter case, the same or different temperature and pressure conditions as those aforementioned can be adopted at these stages. The formed sealed area is cooled, if necessary, under application of pressure by optional means to form a sealed area with good sealing efficiency. For instance, immediately after completion of the heat sealing operation, the heat sealed area in which the resin is still in the softened or molten state is pressed by two positively cooled press bars whereby the resin is solidified. Although any operation known to those skilled in the art to cool and harden the adhesive polymer can be used.

Figure 11:
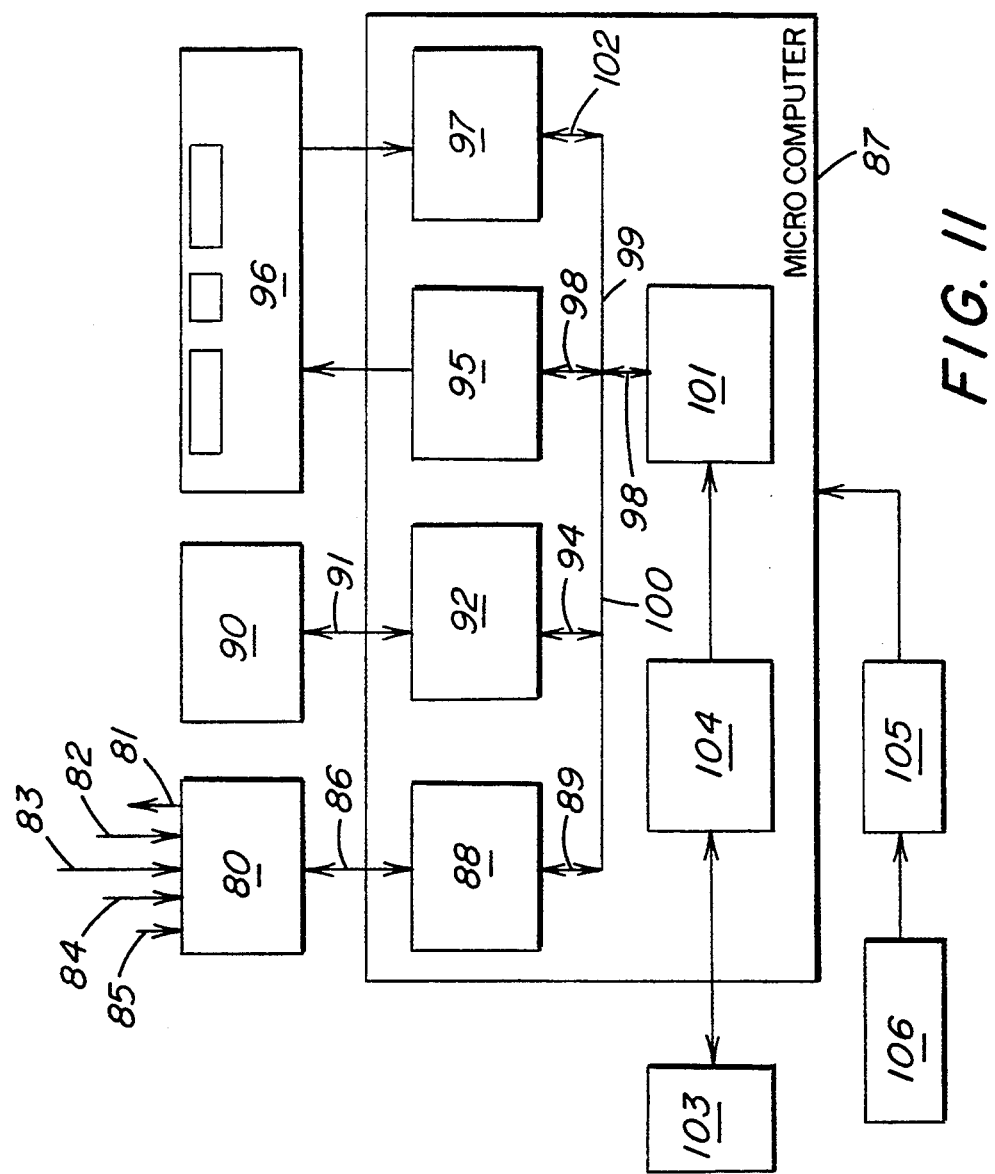
FIG. 11 is a electric block diagram of the analyzer.

FIG. 11 shows the block diagram of the functions and interrelationship of these functions for the analyzer 12 with its electrical connection to the flow cell 16 of FIGS. 1–9. The analog input processing unit 80 of the analyzer 12 interfaces with the electric circuit 50 by the electrical connector 13 to allow signals from the sensors 38 and any temperature detector 61 of previous Figures. Also, the electrical connection allows for electrical current to be supplied to any heater and resistor on board 66 and for any current or voltage that may be needed by the sensors 38 on the board 66. The electrical connections can be separate but are preferably individual connections in a bundle connector or ribbon cable. Connection 81 can carry current to an amperometric oxygen sensor 38 of FIG. 6. Respectively, connections 82, 83, 84, and 85 can carry signal and/or supply current or voltage to: the sensors 38, the thermistor 61, and heater 63 shown in the previous Figures. The processing unit 80 can be electrically connected to the microcomputer 87 by 86 to the function of a 12 bit analog to digital converter 88. Converter 88 can be electrically connected by 89 to line 100, a type of buss line. By line 100 connections are made to unit 101 which has is a date/time circuit and battery backup random access memory device and can be and preferably is an 8 bit central processing unit (CPU) microprocessor 101. In addition the encoded information reader and drive circuit unit 90 is connected by line 91 to the microprocomputer 87 through Input/Output (I/0) port 92 for two way communication. The CPU is connected through I/0 port 95 to the display and keyboard unit 96, and this unit is connected through I/O port 97 and through line 102 to line 100 for communication with the microcomputer 87. The CPU 101 is connected for external communication by RS232 and drive circuit unit 103 through serial port 104. The microcomputer 87 is connected to a power supply 105 and battery pack 106 for power. Although a particular preferred arrangement for the functional units of the analyzer 12 has been specifically set forth variations are possible that may delete one or more of the functional units. As long as the processing unit 80 and converter unit 94 are present when analog signals are used, and a processor is functionally tied into these units and power is supplied and a read out can be obtained the analyzer 12 is usable with the cartridge 11 having flow cell 16 of previous figures. Suitable software resides in the CPU to accomplish these connections and to perform the calibration and analysis of samples.

We claim:

1. Portable multiple sample fluid analyte cartridge for a fluid analyte measuring device, comprising:
   A. housing of the cartridge having the following:
   1) at least one fluid inlet supportively connected to the housing for introduction of fluids to the housing;
   2) flow cell supportively positioned within the cartridge housing having an opening for fluid communication with the inlet and associated with the inlet to receive fluids from the inlet, wherein the flow cell has a channel for fluid flow through the flow cell and from the flow cell at a second opening and having a sensor containment space and a spaced-apart reference electrode containment space and wherein the flow cell also has:
      i) at least one sensor supportively located within the flow cell in the sensor containment space where the sensor is hydrated for sensing contact with fluids in the channel of the flow cell;
      ii) reference electrode located in the reference electrode containment space in conductive contact with a contained quantity of reference fluid for the number of multiple sequential tests for the cartridge where the reference electrode containment space and sensor containment spaces are spaced apart from each other and in conductive relation with each other;
      iii) fluid occupying the channel of the flow cell where the fluid is selected from the group consisting of storage fluid, hydrating fluid, flush solution, calibrating fluid and sample fluid;
      iv) electric circuit means attached for electrical conduction to the sensors and reference electrode and which is electrically isolated from the fluid samples in the channel;
   3) signal conveyor connected to the electric circuit means to transmit signals responsive to the fluids contacting the sensors;
   4) a expandable waste reservoir contained within the cartridge housing and in fluid communication with the flow cell to receive and retain the multiple sequential fluids passed through the flow cell;
   5) at least one flow control means associated with the waste reservoir to retard back flow of the fluids received from the flow cell.

2. Cartridge of claim 1 wherein the flow cell is oriented in the cartridge housing so that the conductive contact between the reference electrode containment area and the sensor contacting the channel of the flow cell are not totally in the same horizontal plane within the housing.

3. Cartridge of claim 1 wherein the flow cell has a reference electrode containment area that is in conductive communication with a sensor and the flow cell is oriented in the cartridge housing with an acute or obtuse angle in relation to the horizontal plane through the cartridge housing.

4. Cartridge of claim 1 wherein the reference electrolyte is a gel.

5. Cartridge of claim 1 wherein the sensor is a Clark cell.

6. Cartridge of claim 1 wherein the sensor is a sensing means.

7. Cartridge of claim 1 wherein the waste reservoir is an expandable bag.

8. Cartridge of claim 1 wherein the waste reservoir is a waste reservoir means.

9. Cartridge of claim 1 wherein the inlet is adapted to receive the needleless fitting of a syringe.

10. Cartridge of claim 1 wherein the sensors are sensor means including thick-film sensors, thin film sensors or both.

11. Cartridge of claim 1, where the sensor has a plurality of different analyte measuring electrodes in the channel to measure blood gases and/or electrolytes.

12. Cartridge of claim 1, where the flow cell has at least two sensors and one is a Clark cell arranged for sensing contact within the channel.

13. Cartridge of claim 1, where the flow cell is oriented in relation to the inlet to facilitate gravity flow through the channel of the fluids introduced at the inlet.

14. Cartridge of claim 1, where the flow control means is a unidirectional valve in the flow path between the flow cell and the reservoir arranged to allow fluid flow from the flow cell to the reservoir and where the valve assists in maintaining fluid in the flow cell to keep the sensor hydrated.

15. Cartridge of claim 14, which includes a second unidirectional valve arranged in fluid communication between the inlet and the flow cell.

16. Cartridge of claim 14, where the valve is a check valve of polycarbonate with a silicone rubber diaphragm.

17. Cartridge of claim 1, where the section of the electrical circuitry in the containment space is printed wiring circuitry connected to the electrodes on a nonconducting substrate and the section leaving the cartridge is a cable means.

18. Cartridge of claim 1, where the cartridge housing has at least one vent for atmospheric gases.

19. Cartridge of claim 1 wherein the sensor includes a measuring electrode and the reference electrode wherein the reference fluid is in constant contact with the reference electrode.

20. Cartridge of claim 19 wherein the reference containment area only communicates with the channel with the at least one sensor for ionic contact between the at least one sensor and the reference electrode.

21. Cartridge of claim 1 wherein the electrodes comprise a Clark cell with an anode and a cathode.

22. Cartridge of claim 1 wherein the reference fluid in contact with the reference electrode remains in contact with the electrode through the multiple sampling at the inlet where the reference fluid is in liquid junction contact through a capillary chamber of the channel or where the reference fluid is a different viscosity or density than fluids in the channel to remain in contact with the reference electrode.

23. Cartridge of claim 22 wherein the liquid junction contact is through a capillary channel from the reference electrode containment area intersects with channel with the at least one sensor.

24. Cartridge of claim 22 wherein a second reference electrode is present in spaced apart relation to the first reference electrode with each reference electrode having a separate channel intersecting with the main channel having the at least one sensor.

25. Portable system for the measurement of at least one analyte in multiple fluid samples, comprising:
  A. a cartridge having:
    1) cartridge housing having the following;
    2) at least one fluid inlet supportively connected to the housing for introduction of fluids including calibrant and optionally flush solution from sources external to the housing;
    3) flow cell supportively positioned within the cartridge housing in fluid flow connection with the inlet and having a flow channel to provide for the flow through of the multiple fluids introduced at the inlet into the flow cell and having a containment space for at least one sensor, where the space is arranged to provide access of the sensor to the channel and to support the sensor in signal processing connection with a signal conveyor in the cartridge housing;
    4) sensors positioned in the flow cell in the containment space and in sensing engagement with the channel for measuring at least one analyte;
    5) signal conveyor connected to the sensor to transmit signals responsive to the fluids contacting the measuring sensor;
    6) a waste reservoir contained within the cartridge housing to receive the fluids passed through the flow cell;
    7) at least one fluid flow control means in fluid communication with the channel of the flow cell at the end away from the inlet and with the reservoir to retard back flow of the fluids from the reservoir;
    8) encoded information carrier for the values of the sensor's performance parameters for later retrieval by a microcomputing means;
  B. calibrator having:
    1) a calibration fluid having a known amount of the one or more analytes to be measured by the sensors for introduction into the inlet and for contact with the sensor to determine a set point for calculating the unknown amount of the one or more analytes to be measured;
    2) encoded information carrier for the values of the calibration fluid information for later retrieval by a microcomputing means when the calibrant is introduced at the inlet of the cartridge and over the sensor in the cartridge;
  C. flush solution for introduction to the inlet of the cartridge to prepare the sensor for the measurement of another sample;
  D. analyzer having:
    1) electronic interpreter for the signals sent from the sensor for the calibrant and for the multiple samples having one or more analytes to calculate the amount of the one or more analytes in the multitude of fluids introduced into the cartridge for measurement;
    2) reader for encoded information to place the encoded information for the sensor and the calibrant into the microcomputing means for use in calculating the values of the amounts of the analytes in the multiple samples introduced into the cartridge;
    3) connector with the signal conveyor of the cartridge;
    4) display means for displaying at least the calculated value of the analyte.

26. Portable system of claim 25 wherein the flush solution is present in a gas impermeable wrapper having a known equilibrated atmosphere for carbon dioxide and oxygen suitable to precondition the electrodes prior to sample introduction.

27. Portable system of claim 25 wherein both encoded information carriers are the same means for encoded information.

28. Portable system of claim 27, where the encoded information means is a bar code.

29. Portable system of claim 25 wherein the calibrant and flush are in a kit.

30. Portable system of claim 25, where the cartridge is packaged in a foil sealed container having a known equilibrated atmosphere for carbon dioxide and oxygen which precondition the electrodes prior to sample introduction and having the encoded information carrier for the cartridge and the kit has the encoded information carrier for the calibrant.

31. Portable system of claim 25 wherein the calibration fluid is introduced into the inlet of the cartridge before each sample fluid.

32. Portable system of claim 25 wherein the cartridge housing has at least one vent for atmospheric gases.

33. Portable system of claim 25 wherein the analyzing means includes a printer means for displaying a hard copy of the calculated values.

34. Portable system of claim 25 wherein the electronic means is a microprocessing means.

35. Portable system of claim 25 wherein the microcomputer means also regulates the temperature of the board and the sample through a heater located in the electric circuit means of the sensor substrate.

36. Method of measuring a multitude of samples having unknown values of known analytes, comprising:
  A. entering into a computer means encoded information of a sensor in a cartridge wherein the cartridge has:
    1) cartridge housing having the following;
    2) at least one fluid inlet supportively connected to the housing for introduction of fluids including calibrant and optionally flush solution from sources external to the housing sources;

3) flow cell supportively positioned within the cartridge housing in fluid flow connection with the inlet and having a flow channel to provide for the flow through of the multiple fluids introduced at the inlet into flow cell and having a containment space for at least one microsensor, where the space is arranged to provide access of the microsensor to the channel and to support the sensor in signal processing connection with a signal conveying means in the cartridge housing;

4) sensors positioned in the flow cell in the containment space and in sensing engagement with the channel for measuring at least one analyte;

5) signal conveying means connected to the sensor to transmit signals which are responsive to analyte concentration in the fluids contacting the measuring sensor;

6) a waste reservoir contained within the cartridge housing and in fluid communication with the valve to receive and retain the fluids passed through the flow cell;

7) at least one flow control means in fluid communication with the flow cell to prevent bi-directional flow of the fluids from the waste reservoir to the flow cell;

B. enter into a microcomputer means encoded information of predetermined analyte values of a calibrant contained in a calibration means having:

1) a calibration fluid having a known amount of the one or more analytes to be measured by the sensors for introduction into the inlet and for contact with the sensor to determine a set point for calculating the unknown amount of the one or more analytes to be measured, 2) means for encoding the values of the calibration fluid information for later retrieval by a microcomputing means when the calibrant is introduced at the inlet of the cartridge and over the sensor in the cartridge;

3) flush solution for introduction to the inlet of the cartridge to prepare the sensor for the measurement of another sample;

C. introducing calibrant into the cartridge that is electronically connected to the microcomputer and analyzing means having:

1) electronic means to interpret the signals sent from the
sensor for the calibrant and for the multiple samples having one or more analytes to calculate the amount of the one or more analytes in the multitude of fluids introduced into the cartridge for measurement;

2) reading means for encoded information to place the encoded information for the sensor and the calibrant into the microcomputing means for use in calculating the values of the amounts of the analytes in the multiple samples introduced into the cartridge;

3) connecting means with the signal conveying means of the cartridge;

4) display means for displaying at least the calculated value of the analyte;

D. introducing sample into the cartridge and obtaining the value of the one or more analytes from the microcomputer and analyzing means;

E. introducing flush solution into the cartridge to clear the previous sample from the flow cell and to maintain the membrane of the sensor in a hydrated state;

F. introducing another amount of calibrant to fill the flow cell to recalibrate the sensor; and G. introducing another sample into the cartridge for testing.

* * * * *